United States Patent
Hutton et al.

(10) Patent No.: US 8,834,527 B2
(45) Date of Patent: Sep. 16, 2014

(54) SYSTEMS AND METHODS FOR MANIPULATING AND/OR INSTALLING A PEDICLE SCREW

(75) Inventors: Clark Hutton, San Clemente, CA (US); Ketchen Smith, Escondido, CA (US); Kai-Uwe Lewandrowski, Tucson, AZ (US)

(73) Assignee: Alphatec Spine, Inc., Carlsbad, CA (US)

(*) Notice: Subject to any disclaimer, the term of this patent is extended or adjusted under 35 U.S.C. 154(b) by 1452 days.

(21) Appl. No.: 11/820,312

(22) Filed: Jun. 18, 2007

(65) Prior Publication Data
US 2008/0082103 A1 Apr. 3, 2008

Related U.S. Application Data

(60) Provisional application No. 60/814,406, filed on Jun. 16, 2006.

(51) Int. Cl.
*A61B 17/70* (2006.01)
*A61B 17/88* (2006.01)
*A61B 19/00* (2006.01)
*A61B 17/02* (2006.01)

(52) U.S. Cl.
CPC ......... *A61B 17/7004* (2013.01); *A61B 17/7079* (2013.01); *A61B 17/7037* (2013.01); *A61B 17/7032* (2013.01); *A61B 17/7034* (2013.01); *A61B 17/8897* (2013.01); *A61B 2019/307* (2013.01); *A61B 17/0218* (2013.01)
USPC .......................... 606/279; 606/105; 606/86 A

(58) Field of Classification Search
USPC ................... 606/60, 246, 250–262, 264–275, 606/277–279
See application file for complete search history.

(56) References Cited

U.S. PATENT DOCUMENTS

| 5,910,141 A | 6/1999 | Morrison et al. |
| 5,984,923 A * | 11/1999 | Breard .......................... 606/259 |
| 6,616,667 B1 * | 9/2003 | Steiger et al. ................. 606/916 |

(Continued)

FOREIGN PATENT DOCUMENTS

| WO | WO 93/11715 A | 6/1993 |
| WO | WO 2005/006948 | 1/2005 |
| WO | WO 2006/042189 A | 4/2006 |

OTHER PUBLICATIONS

International Search Report for Application No. PCT/US2007/014258 dated Dec. 28, 2007.

*Primary Examiner* — Pedro Philogene
*Assistant Examiner* — Lynnsy Summitt
(74) *Attorney, Agent, or Firm* — Michael J. Loi

(57) ABSTRACT

A spinal screw assembly adapted to be secured to a vertebrae for providing securement across at least two vertebrae. The assembly includes a pedicle screw having a substantially spherical head portion, a threaded shaft portion, and an engagement surface in the head portion for driving said screw into the vertebrae, and a body member comprising a tower portion having an open top, a break-away section for manipulation of the screw upon implantation into the vertebrae, a base body at a proximal region of the body member and a break zone which acts as a transition between the base body and the tower portion. A resealably securable setscrew within the body member secures and fully contains the rod within said assembly. The break-away section remains completely outside a wound and is removed or broken off once the screw has been fully assembled inside the vertebrae.

5 Claims, 16 Drawing Sheets

(56) References Cited

U.S. PATENT DOCUMENTS

| | | | |
|---|---|---|---|
| 7,083,621 B2* | 8/2006 | Shaolian et al. | 606/86 A |
| 7,806,913 B2* | 10/2010 | Fanger et al. | 606/260 |
| 7,955,355 B2* | 6/2011 | Chin | 606/246 |
| 8,002,798 B2* | 8/2011 | Chin et al. | 606/246 |
| 8,092,497 B2* | 1/2012 | Pasquet et al. | 606/248 |
| 8,109,975 B2* | 2/2012 | Veldman et al. | 606/257 |
| 8,382,809 B2* | 2/2013 | Kaufman et al. | 606/305 |
| 8,529,602 B2* | 9/2013 | Richelsoph | 606/254 |
| 2003/0199873 A1* | 10/2003 | Richelsoph | 606/61 |
| 2004/0267264 A1* | 12/2004 | Konieczynski et al. | 606/73 |
| 2005/0065517 A1* | 3/2005 | Chin | 606/61 |
| 2005/0085813 A1* | 4/2005 | Spitler et al. | 606/61 |
| 2005/0261687 A1* | 11/2005 | Garamszegi et al. | 606/61 |
| 2005/0273101 A1 | 12/2005 | Schumacher | |
| 2006/0009777 A1* | 1/2006 | Lim et al. | 606/90 |
| 2006/0036244 A1* | 2/2006 | Spitler et al. | 606/61 |
| 2006/0036252 A1* | 2/2006 | Baynham et al. | 606/73 |
| 2006/0036255 A1 | 2/2006 | Pond et al. | |
| 2006/0084993 A1* | 4/2006 | Landry et al. | 606/61 |
| 2006/0111713 A1* | 5/2006 | Jackson | 606/61 |
| 2006/0173454 A1* | 8/2006 | Spitler et al. | 606/61 |
| 2006/0241600 A1* | 10/2006 | Ensign et al. | 606/61 |
| 2006/0247630 A1* | 11/2006 | Iott et al. | 606/61 |
| 2006/0293664 A1* | 12/2006 | Schumacher | 606/61 |
| 2007/0088357 A1* | 4/2007 | Johnson et al. | 606/61 |
| 2007/0093826 A1* | 4/2007 | Hawkes et al. | 606/61 |
| 2008/0161853 A1* | 7/2008 | Arnold et al. | 606/246 |
| 2008/0161863 A1* | 7/2008 | Arnold et al. | 606/319 |

* cited by examiner

SYSTEMS AND METHODS FOR MANIPULATING AND/OR INSTALLING A PEDICLE SCREW

REFERENCE TO RELATED APPLICATIONS

The present application is based upon and claims priority from U.S. Provisional Patent Ser. No. 60/814,406, filed on Jun. 16, 2006, the entire contents of which are herein incorporated herein by reference.

FIELD OF THE INVENTION

The present invention is generally directed to installing and adjusting a spinal screw assembly and, more specifically, to systems and methods for providing an adjustable securement of a fixation rod to or across one or more vertebrae.

BACKGROUND OF THE INVENTION

The spinal column is a highly complex system of bones and connective tissues that provides support for the body and protects the delicate spinal column and nerves. The spinal column includes a series of vertebrae stacked one atop the other, whereby each vertebral body includes a relatively strong bone portion forming the outside surface of the body and a relatively weak bone portion from the center of the body. Situated between each vertebral body is an intervertebral disc formed from a non-bony, fibro-cartilage material that provides for cushioning and dampening of compressive forces applied to the spinal column. The vertebral canal containing the delicate spinal cords and nerves is located just posterior to the vertebral bodies.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of the one vertebra over another, usually in a lumbar or cervical spine) and other disorders caused by abnormalities, disease or trauma, such as ruptured or slipped discs, degenerative disc disease, fractured vertebra, and the like. Patients suffering from such conditions usually experience extreme and debilitating pain as well as diminished nerve function.

Certain spinal conditions as mentioned above, including a fracture of a vertebrae and a herniated disc, indicate treatment by spinal immobilization. Several methods of spinal joint immobilization are known, including surgical fusion and the attachment of pins and bone plates to the affected vertebras.

In an attempt to effectively treat the above-described conditions and, in most cases to relieve pain suffered by the patient, there have been numerous spinal fixation techniques developed to remedy such issues. Nonetheless, as will be set forth in more detail below, there are some disadvantages associated with current fixation techniques and devices. U.S. Pat. No. 6,030,388 (granted Feb. 29, 2000 to Yoshimi, et al.) discusses prosthetic devices used in bone fixation systems, such as those used to treat degenerative and trauma related spinal deformities. This patent discusses a bone fixation element, a linking member and a coupling member having a first channel for receiving a portion of the bone fixation element and a second channel for receiving a portion of the linking member. The channels are oriented within the coupling member such that the central longitudinal axes of the first and second channels are offset with respect to one another. Furthermore, the first and second channels are configured within the coupling member so as to provide for communication of a securing force between the bone fixation element and the linking member such that the bone fixation element is rigidly secured with respect to the linking member.

U.S. Publication No. 2005/0131408 (granted on Jun. 16, 2005 to Sicvol, Christopher W., et al.) discusses delivery and implantation of bone anchors into bone, in particular, one or more vertebral bodies of the spine. This patent discusses a bone anchor having a distal bone engaging portion and a receiving member having a recess for receiving a spinal fixation element. The proximal end of the receiving member may have an arcuate groove formed on an exterior surface thereof to facilitate connection of an instrument to the receiving member.

U.S. Pat. No. 6,802,844 (granted on Oct. 12, 2004 to Ferree) discusses bodies which connect to vertebra to be aligned, and elongated elements that connect to the bodies, which are adjustable relative to the bodies in multiple dimensions. The patent further discusses locking mechanisms that allow the alignment to proceed in an orderly fashion until a desired degree of correction is achieved. Each elongated element has a shaped end terminating in the first portion of the lockable coupling mechanism. The vertebral connector bodies each include a feature for attaching the body to respective vertebrae, and the second portion of the lockable coupling mechanism.

U.S. Pat. No. 5,772,661 (granted on Jun. 30, 1998 to Michelson) discusses a method and instrumentation for performing spinal surgery, including discectomy, interbody fusion and rigid internal fixation of the spine, from the lateral aspect of the spine. This patent discusses a surgical procedure consisting of the removal of spinal material across the disc, fusion, and rigid internal stabilization via the implant may all be performed via the closed space within the extended outer sleeve.

Thus, it is desirable to provide improved systems for internal fixation of adjacent vertebral bodes of the spine. Accordingly, some embodiments of the present invention provide an extended range of motion (as compared to the prior art) for allowing a surgeon additional freedom in locating the screws and easing the assembly process by reducing the requirements for rod contouring. Such embodiments of the present invention minimizes, and in some aspects eliminates, the failures of the prior art, and other problems, by utilizing the structural features described herein. Thus, the result is a significantly improved system and method for manipulating and installing a pedicle screw.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the drawings, subsequent detailed description and appended claims.

SUMMARY OF THE INVENTION

The foregoing and other features, aspects, and advantages of the present invention will be more apparent from the following detailed description, which illustrates exemplary embodiments of the present invention. Some of the embodiments of the present invention relate to a spinal screw assembly for providing an adjustable securement of a stabilization rod between at least two vertebrae. The assembly is preferably used with at least one other such assembly to secure the fixation rod.

In an embodiment of the present invention, a spinal screw assembly adapted to be secured to a vertebrae is provided. The spinal screw assembly includes a pedicle screw having a head, a threaded shaft portion, and an engagement surface in the head portion for driving the screw into the vertebrae. The spinal screw assembly also includes a body member for receiving the head portion of the screw. The body member entails a base from which the threaded shaft portion projects, a tower portion, and a pair of opposed slots therein adapted to receive a portion of a fixation rod therebetween. Provided between the base and the tower portion is a break-away section which allows the tower portion to be removed from the base.

In an embodiment, the spinal screw assembly further details a securable setscrew for threading onto corresponding threads provided adjacent the pair of opposed slots. The setscrew is adapted to bear against a portion of the fixation rod disposed between the pair of opposed slots to secure the fixation rod within the assembly.

In an embodiment, the spinal screw assembly details at least a portion of the break-away section including threads corresponding to threads of the setscrew and threads of the base. The threads of the break-away section allows the setscrew to traverse the break-away section into the base.

In an embodiment of the present invention, a fixation rod is provided. The fixation rod is adapted for securement between at least two spinal screw assemblies. The fixation rod includes a rod body having a predetermined length and one or more engagement portions provided on at least one end of the rod.

In an embodiment, the fixation rod further details engagement portions selected from a group consisting of a depression, an opening, a nib, a protrusion, a clip, a snap ring, a washer and a flared end. The flare portion includes at least a portion of the perimeter of the end. Also, the nib, protrusion or flared end may be integral with the rod. The clip, snap ring and/or washer may be received by a groove machined into fixation rod.

In an embodiment of the present invention, a compressor tool for compressing together at least two vertebrae is provided. The compressor tool includes a shaft having a first end for engaging a screw assembly, and a lever having a first end and a second end. The first end of the lever is movably attached to the first end of the shaft and includes an engagement portion for engaging an end of a fixation rod positioned within the screw assembly when the lever is in a first position prior to compression. The compressor also includes a handle attached to the shaft at a second end opposite the first end.

In an embodiment, the compressor tool further details the lever including a first portion having a first length and being provided adjacent the first end. The first portion is provided at an angle relative to the remainder of the length of the lever. The lever is movably attached to the shaft at a point where the angle of the first portion begins relative to the remainder of the length of the lever.

In an embodiment of the present invention, a nested dilation tube assembly for enabling implantation of a spinal screw assembly into a vertebrae is provided. The dilation assembly includes a plurality of dilation tubes of increasing diameter. Each dilation tube includes an elongated cylindrical shaft with an outer diameter slightly larger than a preceding dilation tube. After being inserting into a body, the plurality of dilation tubes form a nested, concentric assembly enabling an opening placed in the spinal area and/or vertebrae to be enlarged up to the outer diameter of a last dilation tube. The inner dilation tubes are capable of being removed from outer dilation tubes such that the inner diameter of an inner most remaining dilation tube forms a space for receiving instruments and/or assemblies for implantation into a vertebrae.

In an embodiment, the nested dilation tube assembly further includes a wire for forming an initial opening into the spine and/or vertebrae. The plurality of nested dilation tubes fit over the wire and enable an opening in the spine formed by the wire to be enlarged up to the outer diameter of a last dilation tube.

In an embodiment of the present invention, a spinal screw assembly system is provided. The spinal screw assembly system includes a nested dilation tube assembly for enabling implantation of a spinal screw assembly into a vertebrae. The dilation assembly includes a plurality of dilation tubes of increasing diameter, each comprising an elongated cylindrical shaft. Each dilation tube includes an outer diameter slightly larger than a preceding dilation tube. After insertion into a body, the plurality of dilation tubes form a nested, concentric assembly enabling an opening placed in the spinal area and/or vertebrae to be enlarged up to the outer diameter of a last dilation tube. Inner dilation tubes are capable of being removed from outer dilation tubes such that the inner diameter of an inner most remaining dilation tube forms a space for receiving a spinal screw assembly for implantation into a vertebrae. The system also includes spinal screw assembly is adapted to be secured to a vertebrae, which includes a pedicle screw having a head, a threaded shaft portion, and an engagement surface in the head portion for driving the screw into the vertebrae. The spinal screw assembly further includes a body member for receiving the head portion of the screw. The body member includes a base from which the threaded shaft portion projects, a tower portion, a pair of opposed slots therein adapted to receive a portion of a fixation rod therebetween. A break-away section provided between the base and the tower portion allowing the tower portion to be removed from the base subsequent to installation. A compressor tool for compressing together at least two vertebrae is also provided within the system. The compressor tool includes a shaft having a first end for engaging the screw assembly, and a lever having a first end and a second end. The first end being movably attached to the first end of the shaft and including an engagement portion for engaging an end of a fixation rod positioned within the screw assembly when the lever is in a first position prior to compression.

Other objectives and advantages of the present invention will become obvious to the reader and it is intended that these objectives and advantages are within the scope of the present invention.

To accomplish the above and related objectives, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION

Figure 1A:
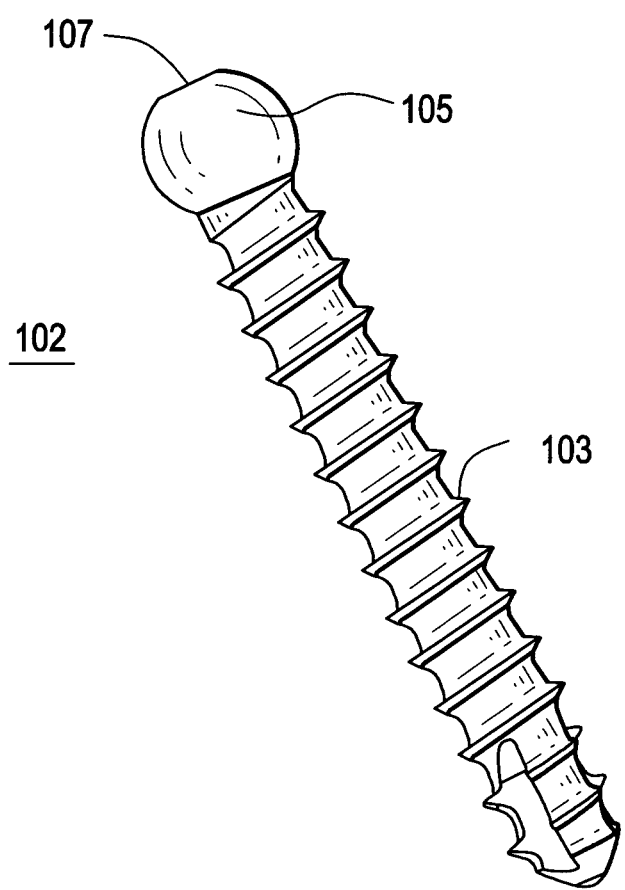
FIG. 1A is a pedicle screw for the use in a spinal screw assembly according to some embodiments of the present invention.

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. These and other embodiments are disclosed or are apparent from and encompassed by, the following description.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways where particular configurations, process steps, and materials disclosed herein as such configurations, process steps, and materials may vary somewhat. In addition, it is to be understood that the phraseology and terminology employed herein are for the purpose of the description and should not be regarded as limiting. Furthermore, as will be apparent to those skilled in the art, the present invention may be embodied in other specific forms without departing from the essential characteristics thereof.

For purposes of the description of the drawings and the embodiments of the present invention, as mentioned for each drawing, each figure may not drawn to scale. Some areas drawn may be bigger and/or simpler in order to clearly portray the improvement to what has already been established. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed. It is also to be understood that the terminology employed herein is used for the purpose of describing particular embodiments only and is not intended to be limiting since the scope of the present invention will be limited only by the appended claims and equivalents thereof.

Referring now in detail to the drawings, the spinal screw assembly 100 of the present invention comprises a pedicle screw 102, a body member 104, a bushing 114 and a setscrew 302 for providing an adjustable securement of a stabilization rod 202 between at least two vertebrae (not shown). The spinal screw assembly 100 is used with at least one other such assembly to secure the fixation rod 202. The present invention allows a pedicle screw 102 to be implanted in a minimally invasive or percutaneous method.

FIGS. 1A-F illustrate perspective views of a spinal screw assembly 100 and its components according to an embodiment of the present invention. FIG. 1A details the pedicle screw 102 which is employed in the assembly 100. The pedicle screw 102 is a cannulated screw (polyaxial or otherwise) design for the purpose of fusing the thoracolumbar spine. The screw 102 is typically intended to cannulate the pedicle, be supplemented by a rod 202 construct, and held in place with a setscrew 302, also referred to as top loaded setscrew, as described below. Pedicle screw 102 is a polyaxial pedicle screw, which typically includes a spherical head portion 105, a threaded shaft portion 103 and an engagement surface 107 in the head portion 105 for use in driving the screw 102 into vertebrae (not shown).

Figure 1B:
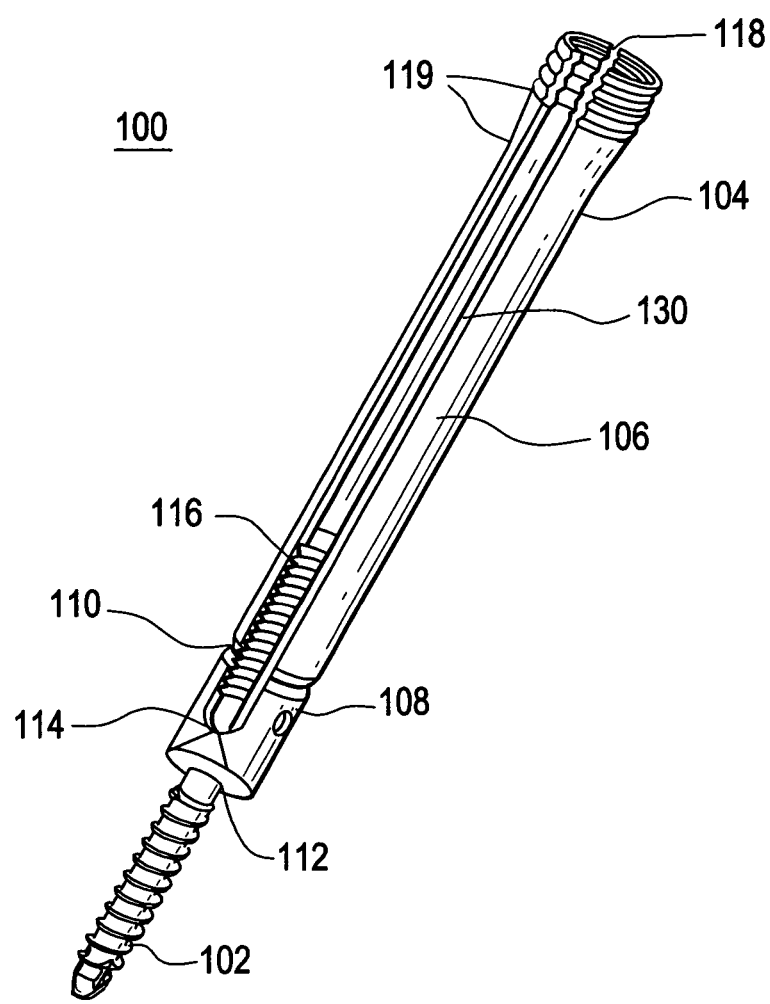
FIG. 1B illustrates a perspective view of a spinal screw assembly and its components according to an embodiment of the present invention.

FIG. 1B details the interaction between the screw 102 and body member 104 of the spine screw assembly 100. The body member 104 includes a high top or tower portion 106, base body 108, break zone 110, threads 116, bushing 114, a pair of opposed parallel slots 130 and additional features 119 for attachment of supplemental devices, as described below. The tower 106 may enable a fully seated (i.e., implanted) screw 102 to be manipulated or aligned, in multiple directions. In particular, the tower 106 allows such functionality from outside the wound (not shown). The tower 106 is constructed preferably of a breakable web of material, which allows the tower 106 to be easily removed (e.g., the web of materials are broken) from the body member 104 at the break zone 110. The break zone 110 is included at the transition of the tower 106 and the base body 108. The top tower 106 acts as a break-away section in that, once the screw 102 has been fully assembled, in which the spine screw assembly is locked via the setscrew 302, the top portion 106 is removed or broken off. In a preferred embodiment, after the tower 106 has been removed, or broken off, the assembly 100 sit flush with the wound, where no protruding components remain outside of the wound. Alternatively, the components could remain below the wound as well, which is understood by one of ordinary skill in the art.

The tower 106 may be threaded 116, in which the thread 116 is clocked in time to the threaded shaft 103 of the screw 102. Using a continuous thread allows for the setscrew 302 to reduce a rod 202 from tower 106 to the base body 108 for stabilization of a fixation rod 202. The tower 106 further includes an open top 118 to aid in visualization and allow uninterrupted access down the body member 104.

Figure 1C:
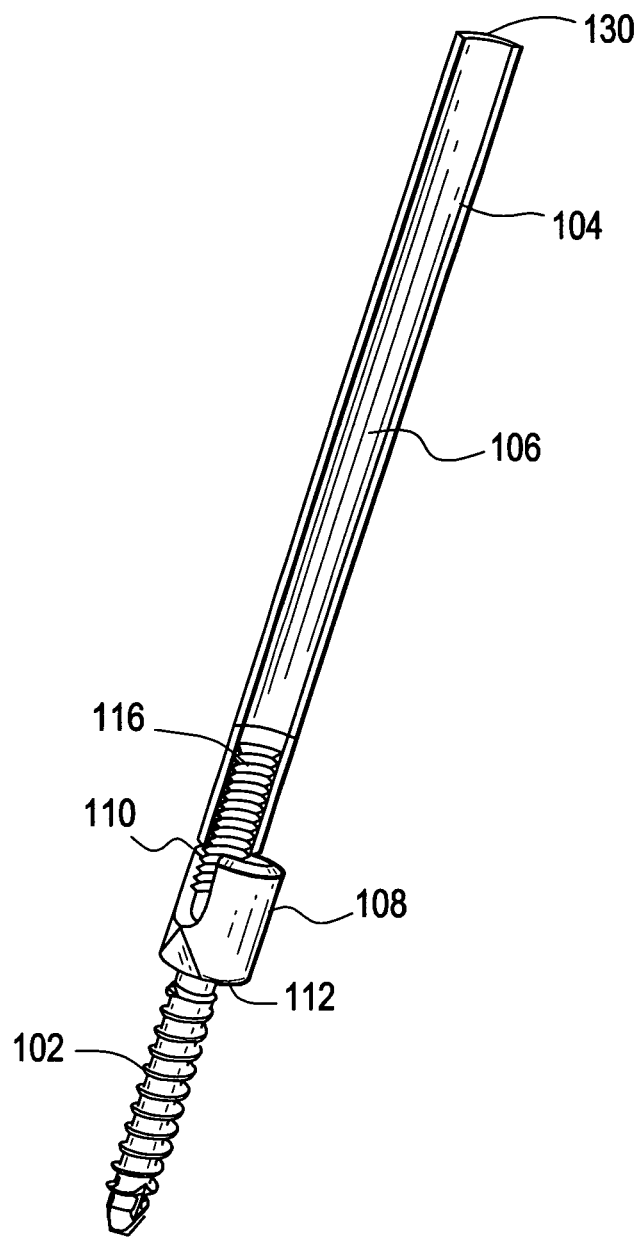
FIG. 1C illustrates a fragmented perspective view of the spinal screw assembly and its components according to an embodiment of the present invention.

FIG. 1C illustrates a fragmented perspective view of the spinal screw assembly and its components according to an embodiment of the present invention. This fragmented view shows that the threaded transition 116 exists between the transition of the tower 106 and the base 108 through the break zone 110. The threaded transition 116 that exists between the tower 106, base 108 and break zone 110 correspond to threads 304 of the setscrew 302. The threads 116 of the break-away section 110 allow the setscrew 302 to traverse the break-away section 110 into the base 106.

Additionally, as discussed below in relation to FIGS. 5A-E, the tower 106 includes additional features 119 (e.g., threads) at the top of the tower 106 to attach screwdrivers 504, alignment jigs, and other supplemental devices to engage the spine screw assembly into vertebrae.

Figure 1D:
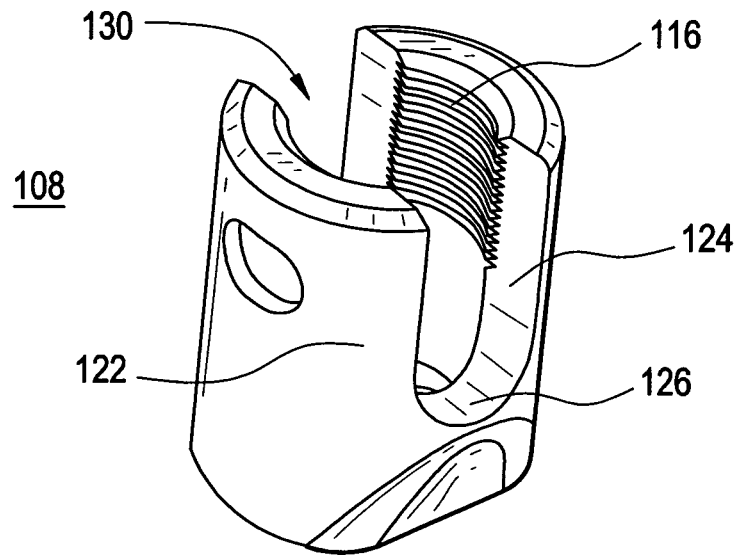
FIGS. 1D-F are fragmented perspective views of the spinal screw assembly according to an embodiment of the present invention.
Figure 1E:
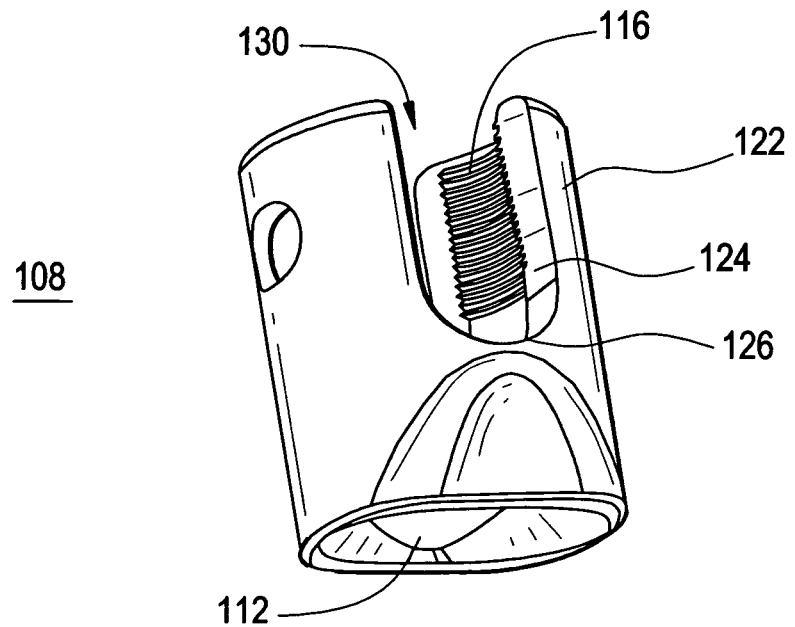
Figure 1F:
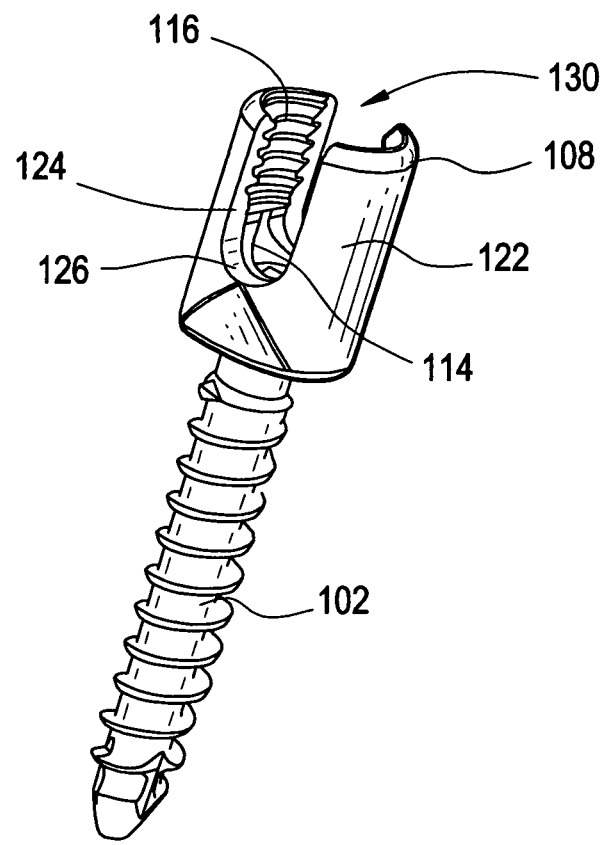

FIGS. 1D-F illustrate the components of the base body 108 of the body member 104 where the stabilization of the fixation rod 202 and screw 102 occurs. The outer or upper interior surface of side walls 122 of the base body 108 both have radially projecting serrations formed therein defining the plurality of axially aligned threads 116. The base body 108 shows the pair of opposed parallel slots 130 axially disposed in the side wall 122 thereof, which terminate at their lower ends in curvilinear surfaces 126. The parallel slots 130 are sized to receive the fixation rod 202 therein, as shown below, with the walls 124 defining the slots 130. The slots 130 extending upwardly beyond the break zone 110 up to the distal end of the tower portion 106 may be inclined slightly to provide a slight holding force on the rod 202 prior to securing the rod 202 with the setscrew 302. The pair of opposed parallel slots 130 are adapted to receive a portion of the fixation rod 202 as a setscrew 302 bears against the fixation rod 202 to releasably secure the rod 202 within the assembly 100, as described below. Alternatively, a surgeon may exert a slight downward force on the rod 202, snapping the rod 202 into the transverse channel defined by the aligned slots 130.

The head portion 106 of the screw 102 is typically positioned in a body member 104 adjacent a curvilinear surface 126 disposed about an aperture 109 in the end of the base body 106, such that the threaded shaft portion 103 of the screw 102 extends therethrough and the curvilinear inner surface 126 abuts and mates with the head portion 105 of the screw 102 so as to define a ball joint therewith. The rounded head surface of the head portion 105 rests upon and mates with a rounded interior surface formed in the inner or lower end of the base body so as to form a modified ball joint that provides the desired variable angular movement of the body member with respect to an embedded pedicle screw 102. The threaded shaft portion 103 of screw 102 extends therefrom through the opening 112 in the lower end of base body 108, as pictured in FIG. 1F.

A bushing 114 is preferably employed within the base body 108 adjacent to the side walls 122 to better distribute the longitudinal forces exerted on the pedicle screw 102; thereby the bushing 114 provides a seat for the fixation rod 202. The bushing 114 further provides flexibility therein and may provide tapered end surfaces adapted to abut opposed sides of the head portion 105. The bushing 114 is positioned within the base body 108 of the body member 104 and outwardly adjacent to the head portion 105 of said screw 102. The bushing 114 further abuts the head portion 105 of the screw 102 upon the setscrew 302 pressing against a portion of the fixation rod 202 whereby the force exerted on the head portion 105 is distributed about the head portion 105.

To provide a basic stability to the system during initial assembly, the bushing 114 can be configured to provide a press fitment about the head portion 105 so that the pedicle screw 102, body member 104 and bushing 114 will not move freely prior to the insertion and securement of the fixation rod 202.

In another embodiment of the invention, the bushing 114 may not be employed. The opposed axial slots 130 in the side wall 122 of the body member 104 of the assembly 100 define a seat for the fixation rod 202. When the setscrew 302 is pressed into the body member 104 with the fixation rod 202 extending thereacross, the planar bottom surface abuts the fixation rod 202 and, in this instance, presses the rod 202 against the upper end of the head portion 105 of the pedicle screw. For such applications, the body member 104 and pedicle screw 102 would be sized such that the upper part of the head portion 105 of the screw 102 would project above the bottom of the seat defined by the axially opposed slots 130 so as to enable the rod 202 to press against the screw 102 and create a rigid, yet adjustable, securement between the body member 104 and the pedicle screw 202.

Figure 2:
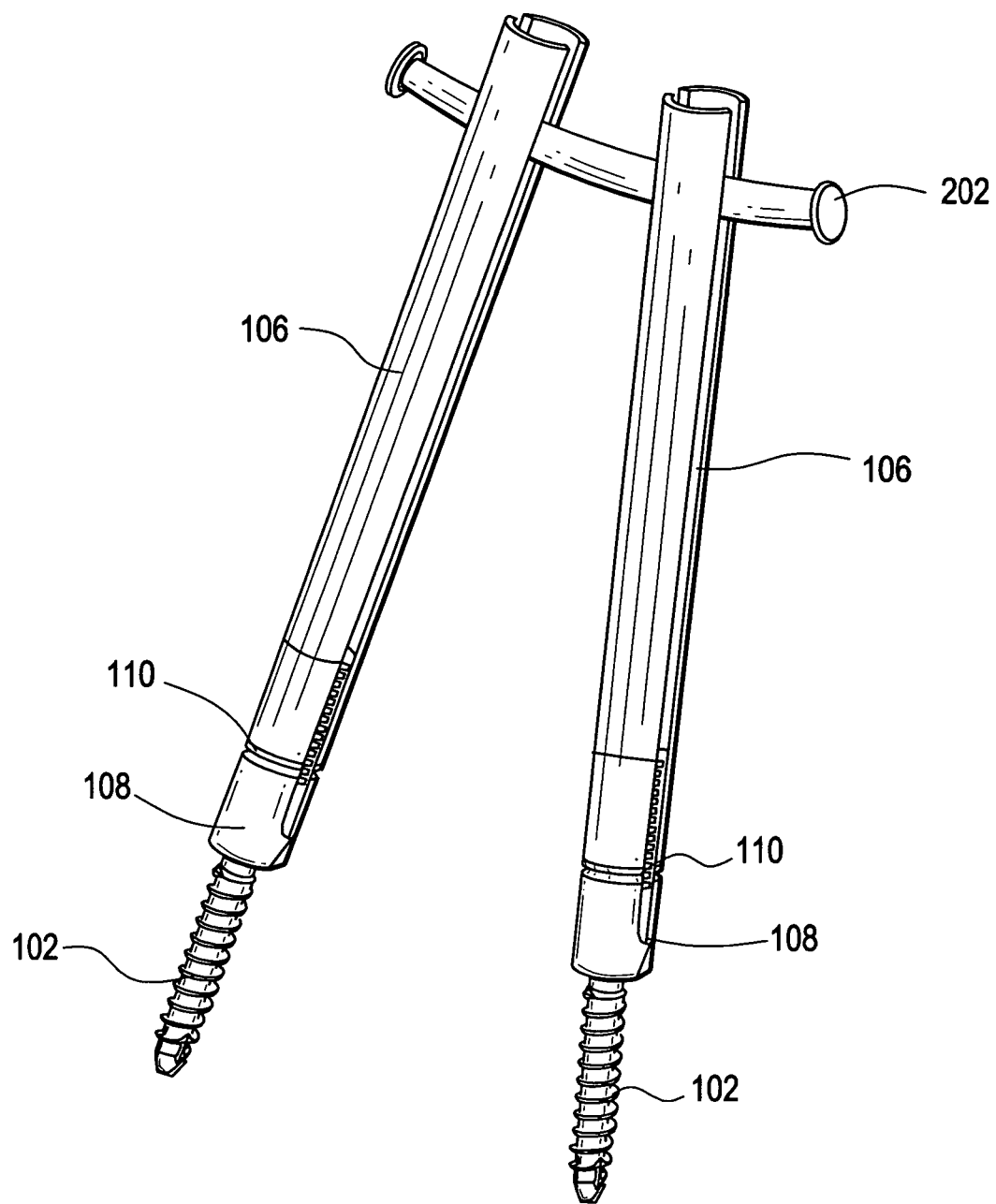
FIG. 2 illustrates a perspective view of a plurality of polyaxial screw assemblies according to an embodiment of the present invention, with a rod traversing therethrough.

FIG. 2 illustrates a perspective view of a plurality of polyaxial screw assemblies 100 according to an embodiment of the present invention, with a rod 202 traversing therethrough. The fixation rod 202 enters the body member 104 through each pair of slots 130. The fixation rod 202 traverses down the body member 104 until it becomes fully seated within the parallel slots 130 of each body member 104, as pictured below in relation to FIG. 3. The fixation rod 202 may traverse each body member 104 though force applied by a surgeon, through force applied by a setscrew 302 pushing the rod 202 down the body member or other means, which would be recognized by one with skill in the art.

Figure 3:
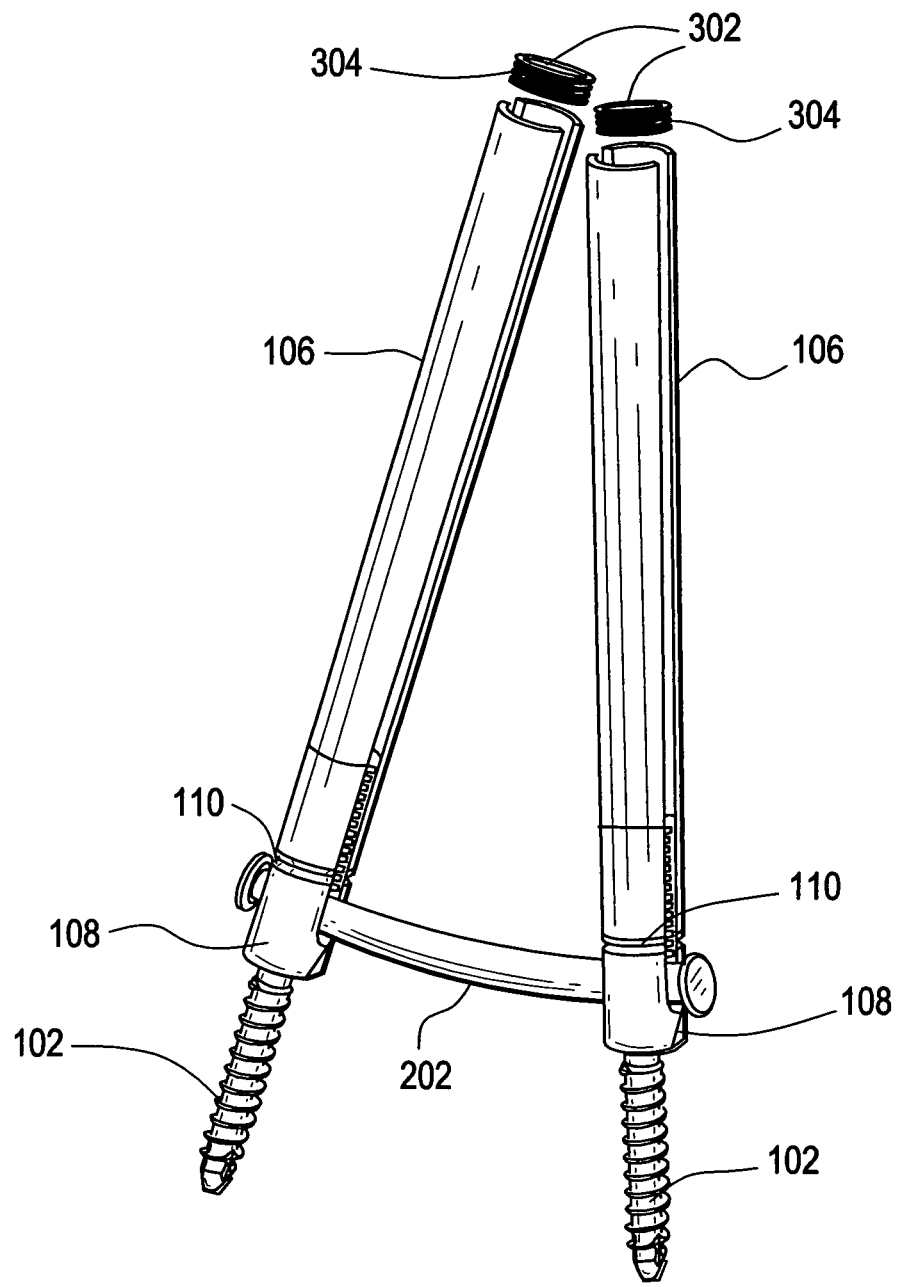
FIG. 3 is a perspective view of a plurality of polyaxial screw assemblies according to an embodiment of the present invention, with a rod having traversed therethrough.

FIG. 3 is a perspective view of a plurality of polyaxial screw assemblies 100 according to an embodiment of the present invention, with a rod 202 having traversed therethrough. After affixation of the rod 202 within the screw assemblies 100, setscrews or setscrews 302 are utilized to lock the fully seated rod 202 in place within the body member 104. The setscrew 302 includes threads 304 to engage the threaded portion 116 of the body member 104. Accordingly, the threaded portion 116 of the body member may be just a portion of the body member 104 or the entire body member 104. The interlocked threads 304 of the setscrew 302 may allow the surgeon to tighten the clamping force on the fixation rod 202 by simply pressing downwardly on the setscrew 302. The threads 304 will hold the component parts in place. To adjust or remove the rod 202, the setscrew 302 is simply rotated 90 degrees about its longitudinal axis, whereupon the threads 304 of the cap 302 are aligned with the open slots 130 in the body member 104, allowing the cap 302 to be simply pulled upwardly away from the fixation rod 202. An engagement slot is provided in the top portion of cap 302 to facilitate the rotation of the setscrew with a suitably sized mating tool (not shown), which is well known in the art.

Figure 4A:
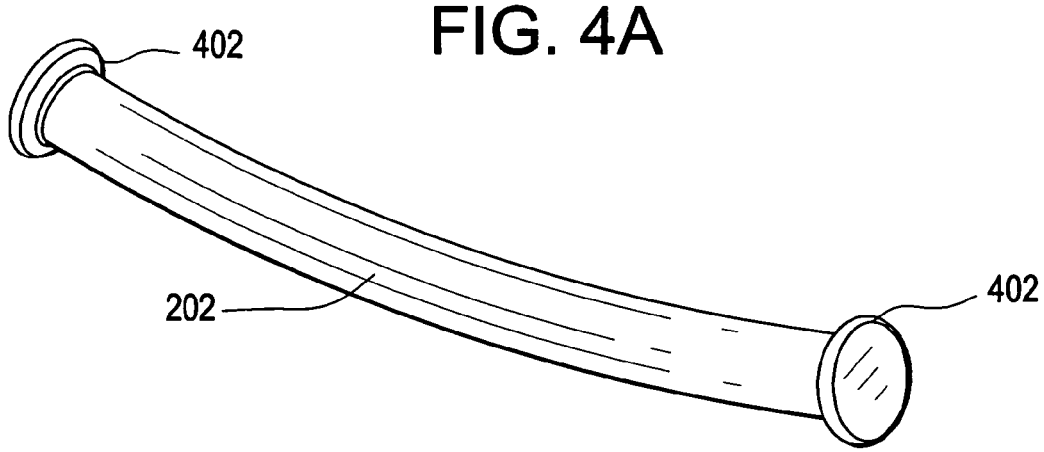
FIGS. 4A-C illustrate extruded features at ends of the fixation rod in accordance with some embodiments of the present invention.
Figure 4B:
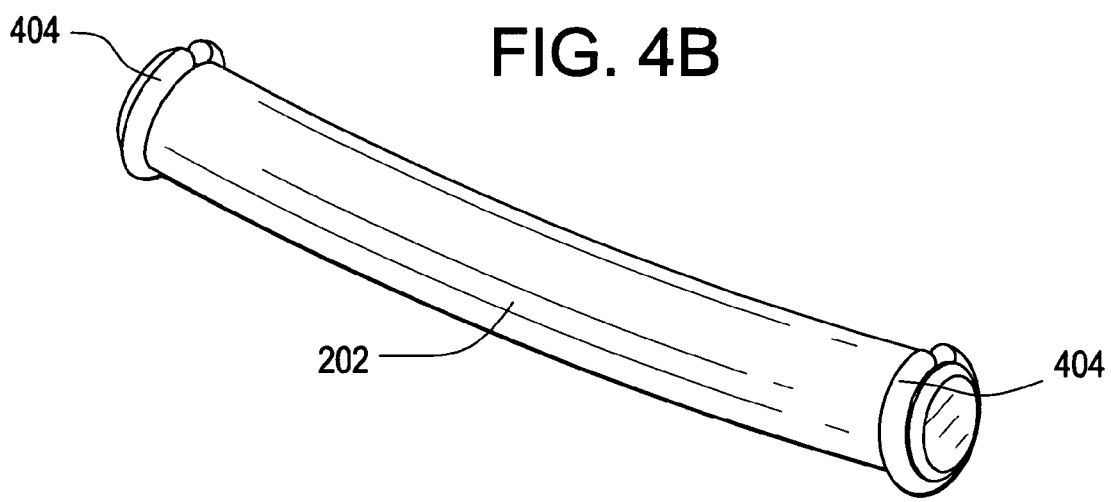
Figure 4C:
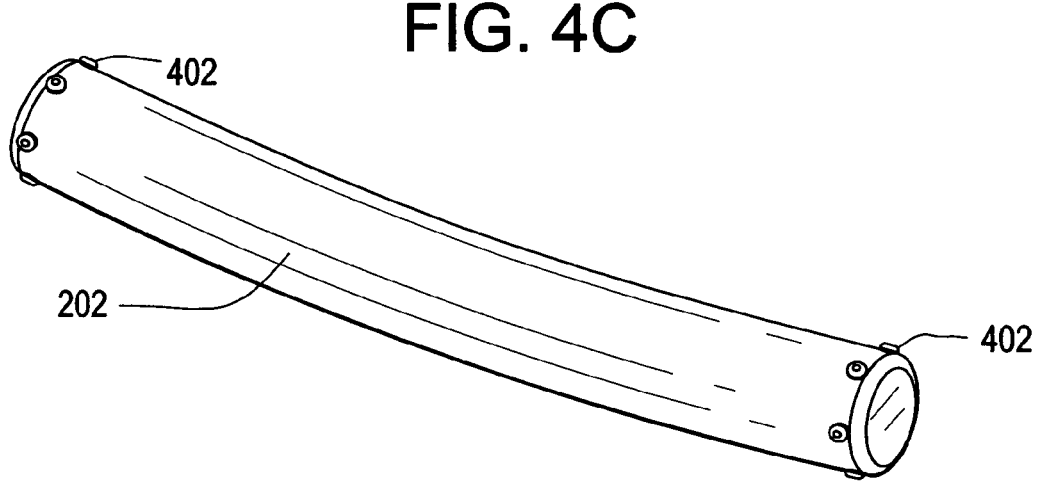

FIGS. 4A-C illustrate extruded features at ends of the fixation rod in accordance with embodiments of the present invention. The fixation rod 202 may embody extruded features at the ends of the rod 202. These features are configured to receive a corresponding engagement portion of a compression tool 600 for moving the fixation rod 202 relative to a spinal screw assembly 100 when the spinal screw assembly 100 is affixed to the vertebrae, as discussed below in relation to FIGS. 6A-6C. As illustrated in FIG. 4A, the fixation rod 202 includes pegs, short spikes, nibs, washers, or flared portions 402 protruding on the distal ends. The flared portions 402 may include at least a portion of the perimeter of the end of the fixation rod 202. In FIG. 4B, the fixation rod 202 includes snap ring clips 404 sitting in grooves, depressions or openings (not shown) machined into the distal ends at a proximal portion of the rod 202. FIG. 4C depicts the features of FIG. 1, the pegs or short spikes 402 being machined into the fixation rod 202 as one piece. The above identified machined and extruded features appended to the fixation rod 202 provide the benefits for use by a surgeon. The rod 202 is fully contained within the body member 104 by the setscrew 302. The rod 202 also need not be tilted or the body member 104, including the towers 106, stretched to allow the rod 202 to be placed into a fully seated position. Furthermore, these above identified features of 402 and 404 allow other instruments to interact with the spine screw assembly 100, as discussed below in relation to FIGS. 6A-6B, as well as other embodiments which would be recognized by one skilled in the art.

Figure 5A:
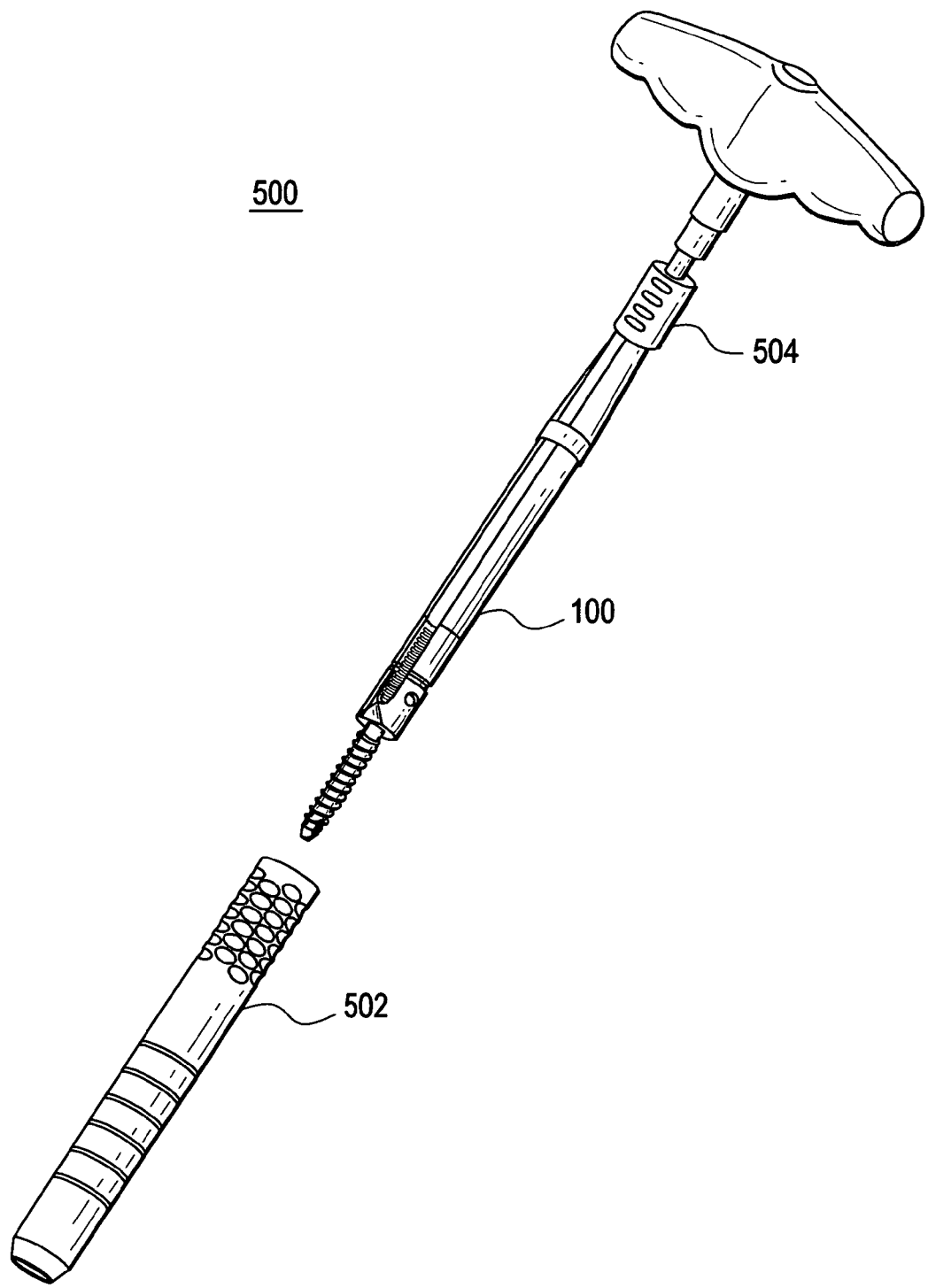
FIGS. 5A-E illustrate the features and assembly according to a dilation instrument according to some embodiments of the present invention.
Figure 5B:
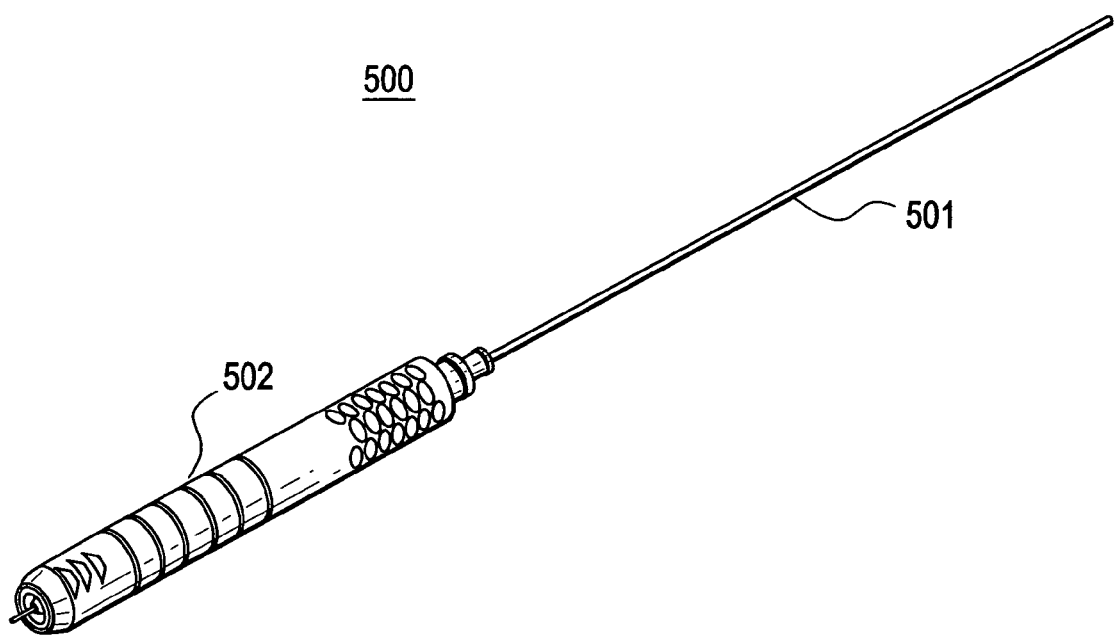
Figure 5C:
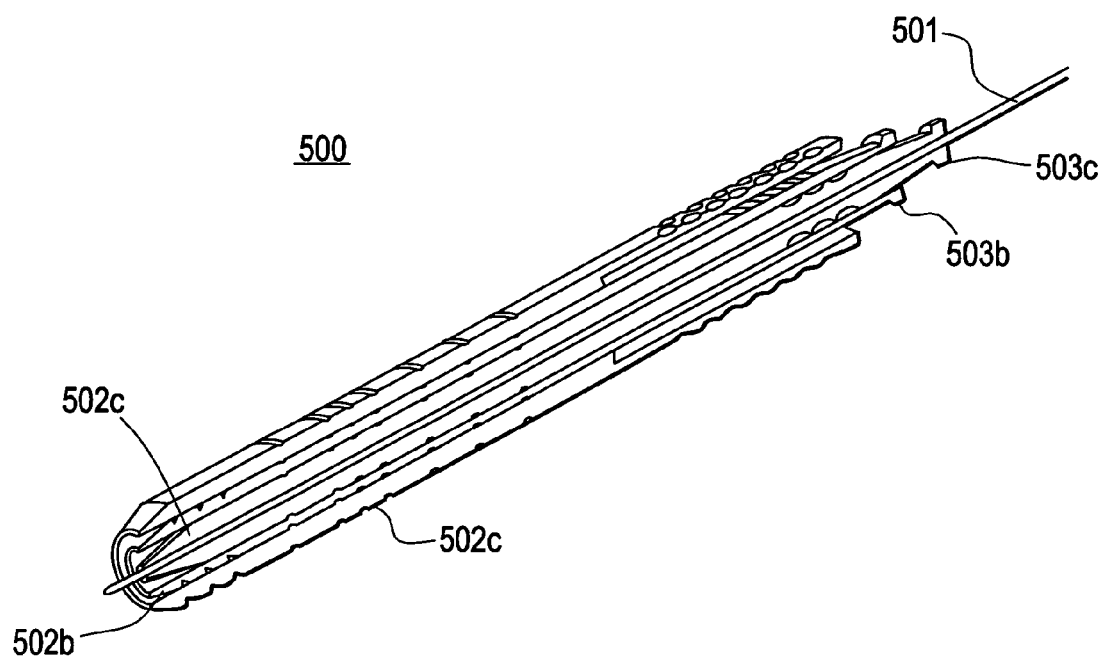
Figure 5D:
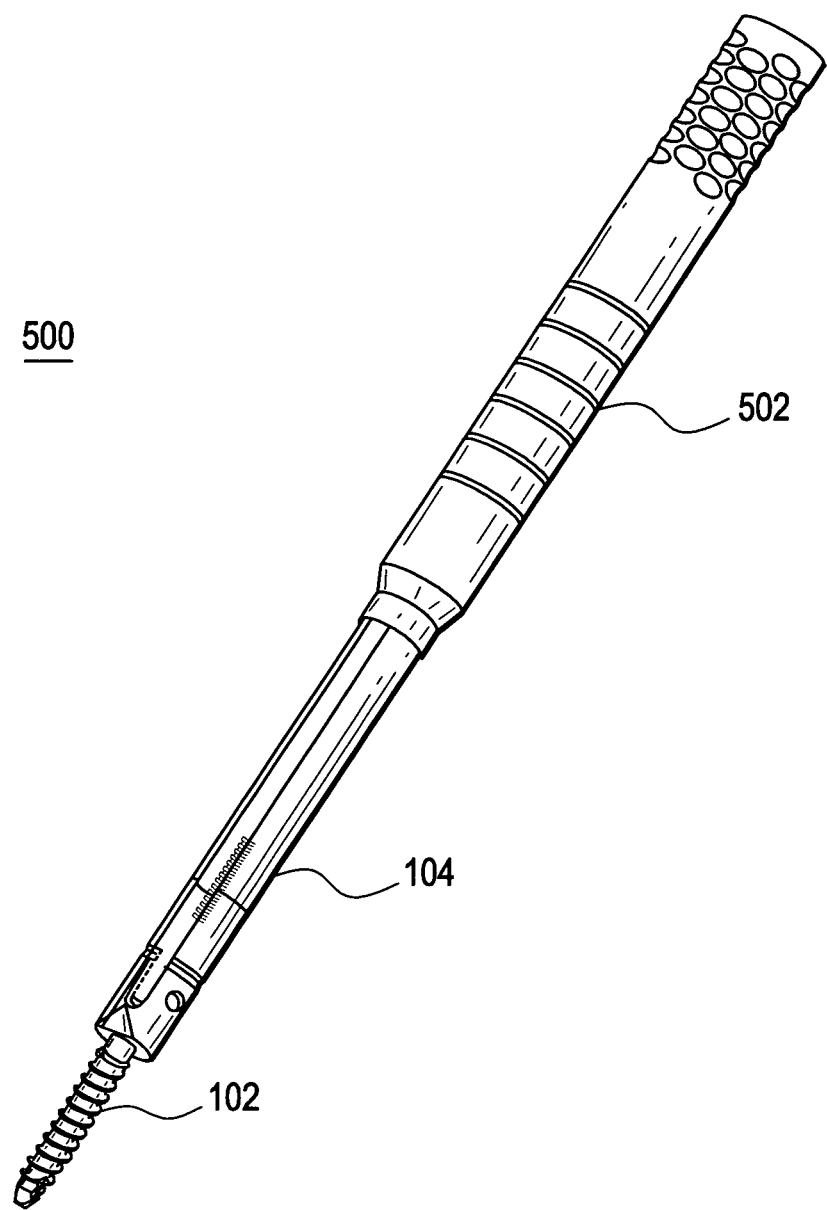
Figure 5E:
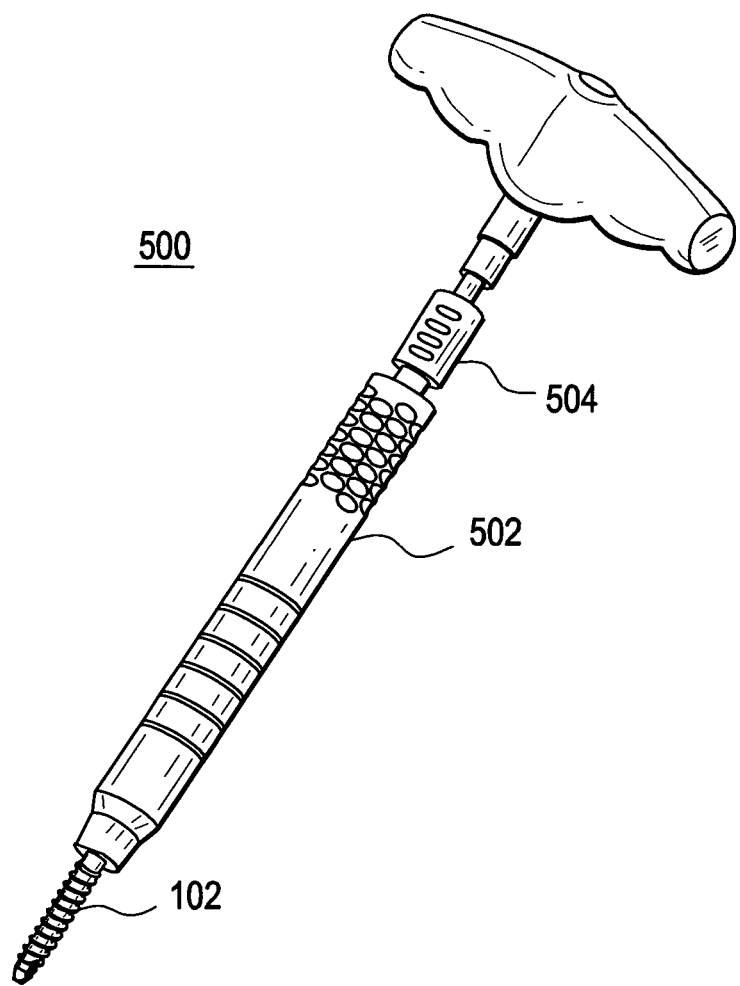

FIGS. 5A-E illustrate the features and assembly according to a nested dilation tube assembly 500. FIG. 5A illustrates the components utilized in the nested dilation tube assembly 500 in accordance with the spine screw assembly 100. As pictured the screw driver 504 (or any other type of mating tool) engages the body member 104 atop the tower portion 106 via the additional features 119 (e.g., threads). The screw 102 and body member 104 enter the dilator 502 (or tube) and thereby engage the vertebrae in accordance with the embodiments of the present invention. As shown in FIG. 5B, the dilation assembly 500 allows the surgeon to use a small wire 501 and progressively dilate the vertebrae (not shown) with increasingly greater diameter dilators 502. As shown in FIG. 5C, once the smaller diameter dilator 502a has been implanted, larger diameter dilators 502b and 502c are implanted, respectively. Upon increasing the diameter of the dilators 502 by implanting a dilator 502 with a greater diameter, previously implanted dilators 502 with smaller diameters may be removed, thereby increasing the opening in the vertebrae; hence, once the largest tube 502c is utilized, the inner tubes 502a and 502b can be removed. The dilation tubes 502 after being inserted into a body form a nested, concentric assembly 500 enabling an opening placed in the spinal area and/or vertebrae to be enlarged up to the outer diameter of a last dilation tube 502c. It can be recognized that one skilled in the art, that the smaller diameter tubes 502 may be removed after each increase in diameter, or all together at the end, after the largest diameter tube is employed. Interior dilation tubes 502a and 502b entail a lip area as flared protrusions 503a and 503b from the distal end of each tube. The protrusions 503a and 503b allow for removal of each tube accordingly. The protrusions 503a and 503b also prevent the tubes 502a and 502b from entering the assembly 500 beyond a predetermined point. It would also be recognized by one of ordinary skill in the art that a variety of number of dilation tubes 502 could be utilized within assembly 500. FIG. 5D depicts the components of the tube 502, body member and screw 102 as discussed above. As illustrated in FIG. 5E, upon employment of the largest diameter tube 502, the screw assembly 100 is implanted through the tube 502 via the use of the screw driver 504.

Figure 6A:
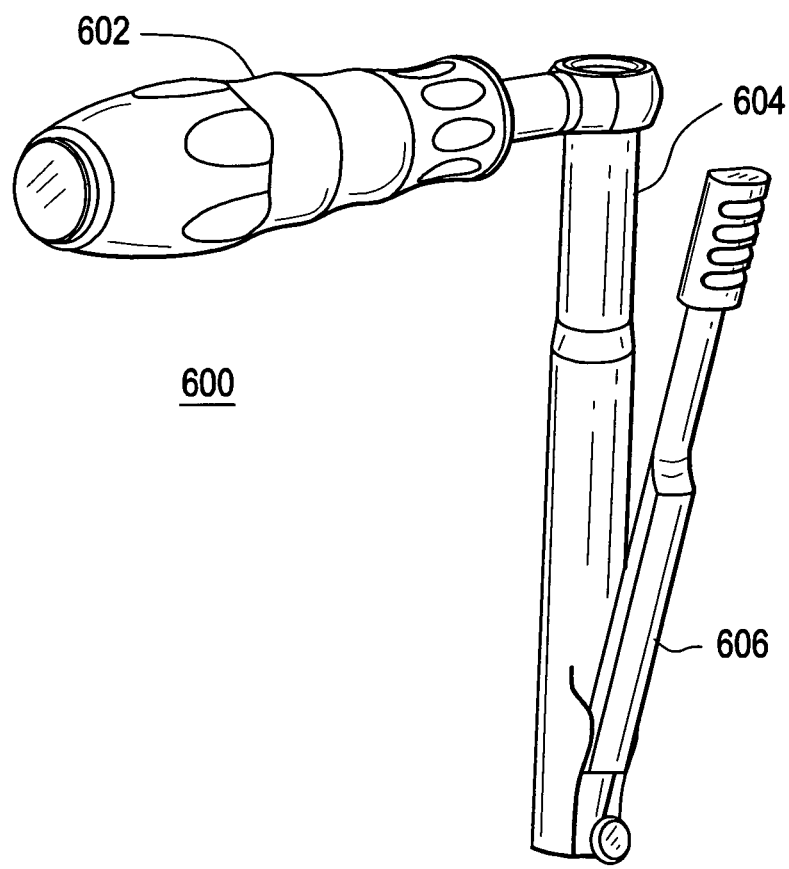
FIGS. 6A-C illustrate the features and assembly according to a compression instrument according to some embodiments of the present invention
Figure 6B:
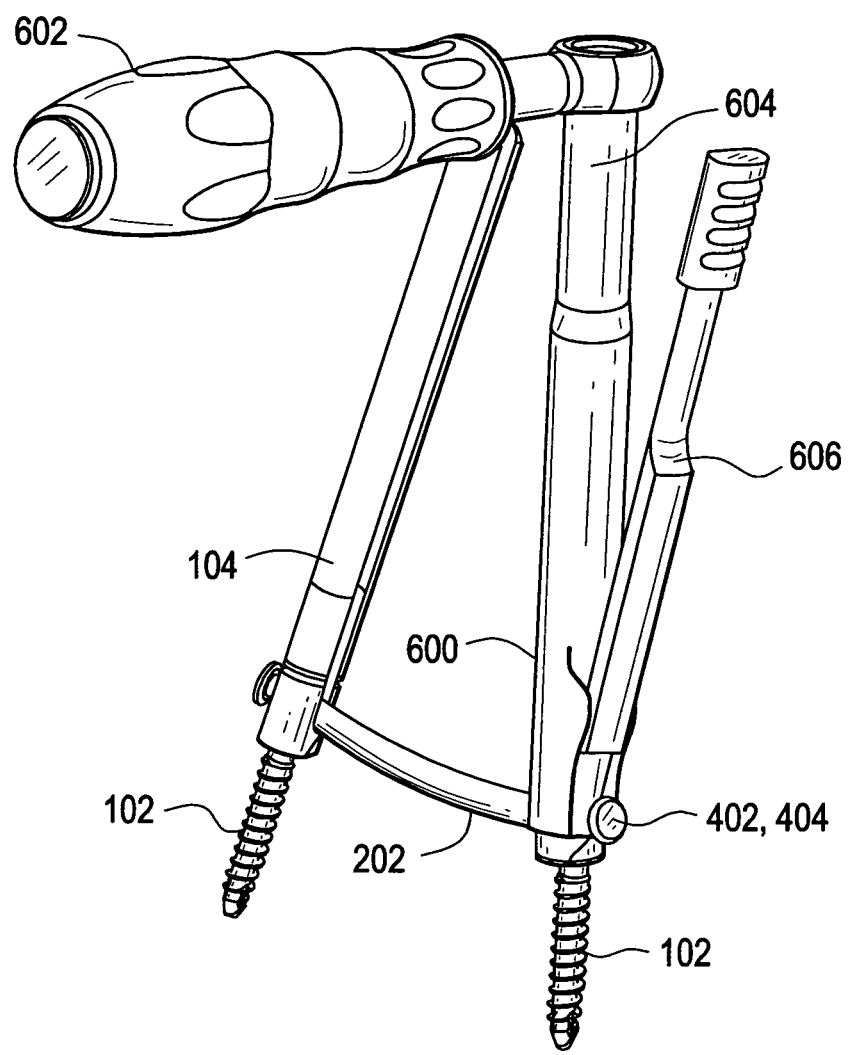
Figure 6C:
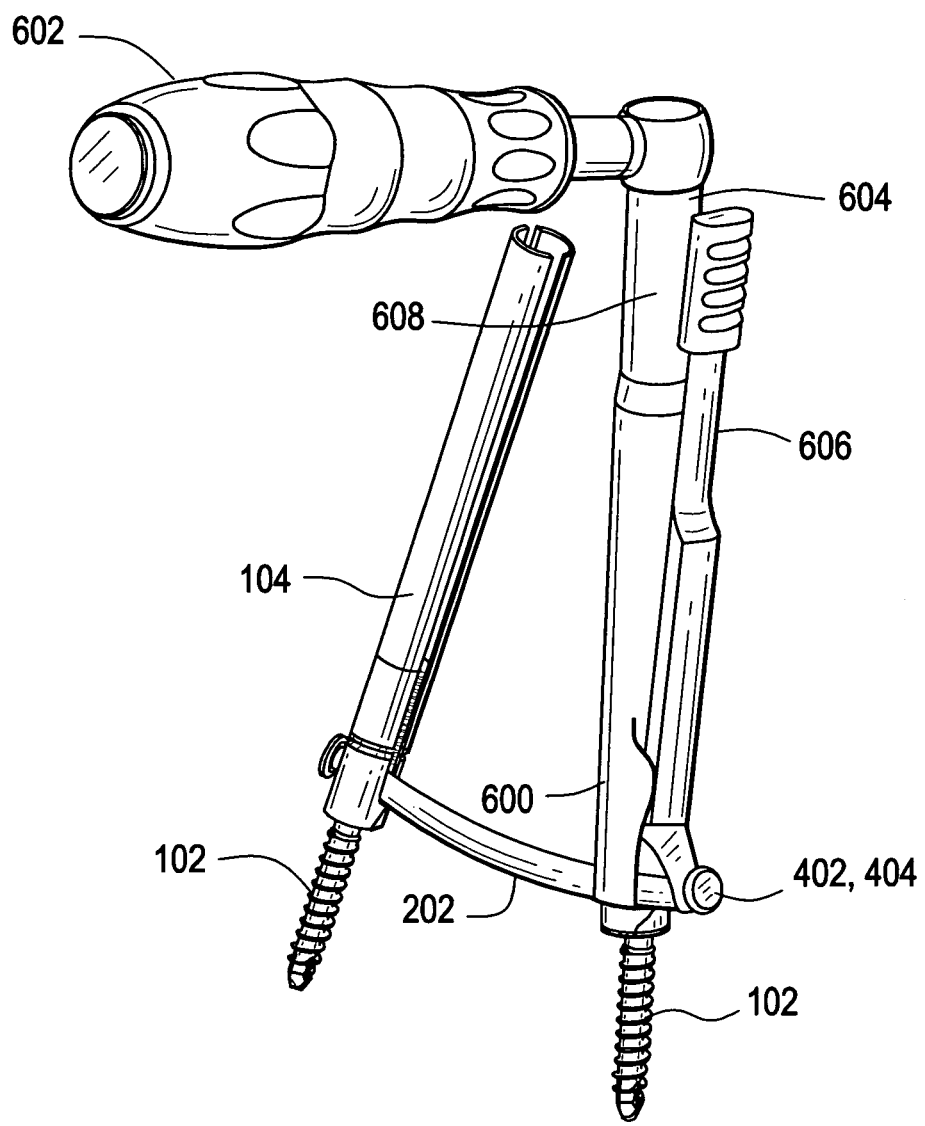

FIGS. 6A-C illustrate the features and assembly according to a compression embodiment of the present invention. FIG. 6A illustrates the compressor 600 including a handle 602, body shaft 604 and lever 606. The lever 606 includes a first end being movably attached to the first end of the shaft 604 and including an engagement portion (not shown) for engaging an end of a fixation rod 202 positioned within the screw assembly when the lever is in a first position prior to compression, and a second end utilized for compression 600. Lever 606 further includes a portion having a first length and being provided adjacent the first end. The first portion is provided at an angle relative to the remainder of the length of the lever 606. The lever 606 is movably attached to the shaft 604 at a point where the angle of the first portion begins relative to the remainder of the length of the lever 606. The shaft 604 connects the handle 602 and the lever 606 and embodies a cylindrical shape adapted to slide over and down the spinal screw assembly 100. The shaft 604 may entail a substantially tubular shape that allows the shaft 604 to receive at least a portion of a screw assembly 100 therein.

FIG. 6B illustrates the compressor 600 including the handle 602 located in conjunction with the distal end of the body member 104 atop the tower portion 106 and the lever 606 positioned in conjunction with the fixation rod 202 which is fully seated in the screw assembly 100. The compressor 600 is positioned adjacent to the body member 104 and above the fixation rod 202, therein the compressor 600 grabs hold of a protrusion of the fixation rod 202, as discussed above in relation to FIGS. 4A-4C and elements 402 and 404. As illustrated in FIG. 6C, a load is applied to the fixation rod 202 by manipulating the level 606 of the compressor 600 and thereby applying a load to the fixation rod 202. To provide balance or leverage upon applying the load to the fixation rod 202, the surgeon can grip onto the handle 602. The fixation rod 202 is displaced within the assembly 100 a distance up to a 5 mm range upon increasing the applied load by a lever depression 608, whereby the distance between a screw assemblies is decreased. Once the desired compression is achieved, the setscrew 302 is finally tightened upon the fixation rod 202 whereby the displacement and compression are preserved.

As described in FIGS. 5A-E and 6A-C, after dilation and compression occurs, it would be understood by one of ordinary skill in the art that the tower portion would be broken off, as described above, thereby creating a fully seated and implanted assembly.

While illustrative embodiments of the invention have been described above, it is, of course, understood that various modifications will be apparent to those of ordinary skill in the art. Such modifications are within the spirit and scope of the invention, which is limited and defined only by the appended claims.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A method for compressing at least two vertebrae together, comprising:
   securing a first spinal screw assembly to a first vertebra;
   securing a second spinal screw assembly to a second vertebrae;
   receiving a portion of a fixation rod in each spinal screw assembly, wherein a first end of the fixation rod includes a first flared portion for positioning adjacent the first spinal screw assembly and wherein a second end of the fixation rod includes a second flared portion that is positioned adjacent the second spinal screw assembly;
   coupling a first end of a compressor tool to the second screw assembly;
   engaging a second end of the compressor tool with the second flared portion; and
   pulling the second flared portion of the fixation rod, wherein the second flared portion of the fixation rod moves relative to the second screw assembly moving in a direction away from both the first and second screw assemblies, and wherein a distance between the first screw assembly and the second screw assembly is decreased.

2. The method of claim 1, further comprising positioning a bushing within a base of a body member, the bushing defining a seat for a portion of the fixation rod.

3. A method comprising:
   attaching a first screw to a first vertebra;
   coupling a first rod receiving member to the first screw;
   inserting a first end of a spinal rod through a first pair of slots in the first rod receiving member, wherein the first end terminates in a first coupling feature that includes at least one of a clip, a snap ring, and a washer adjacent the first rod receiving member;
   attaching a second end of the spinal rod to a second vertebra;

attaching a first end of a compressor tool to the first rod receiving member;
coupling a second end of the compressor tool to the first coupling feature; and
pulling the spinal rod through the first pair of slots using the second end of the compressor tool.

4. The method of claim 3, wherein the step of attaching the second end of the spinal rod to a second vertebra comprises:
attaching a second screw to the second vertebra;
coupling a second rod receiving member to the second screw; and
inserting the second end of the spinal rod through a second pair of slots in the second rod receiving member, wherein the second end terminates in a second coupling feature adjacent the second rod receiving member.

5. The method of claim 3, further comprising pulling the first end of the spinal rod through the first pair of slots to position the second vertebra relative to the first vertebra.

* * * * *